US 7,129,836 B2

(12) United States Patent
Lawson et al.

(10) Patent No.: US 7,129,836 B2
(45) Date of Patent: Oct. 31, 2006

(54) WIRELESS SUBJECT MONITORING SYSTEM

(75) Inventors: Corey J. Lawson, Sussex, WI (US); David W. Duckert, Menomonee Falls, WI (US); David G. Hernke, Sussex, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 504 days.

(21) Appl. No.: 10/668,569

(22) Filed: Sep. 23, 2003

(65) Prior Publication Data

US 2005/0075067 A1    Apr. 7, 2005

(51) Int. Cl.
*G08B 1/08* (2006.01)

(52) U.S. Cl. .............. 340/539.12; 340/531; 340/539.1; 340/539.11; 340/573.1; 705/2; 705/3

(58) Field of Classification Search ........... 340/539.12, 340/531, 539.1, 539.11, 573.1, 573.4, 286.07, 340/825.19; 705/2, 3
See application file for complete search history.

(56) References Cited

U.S. PATENT DOCUMENTS

| | | | |
|---|---|---|---|
| 5,003,984 A | | 4/1991 | Muraki et al. |
| 5,446,678 A | | 8/1995 | Saltzstein et al. |
| 5,452,356 A | | 9/1995 | Albert |
| 5,481,255 A | | 1/1996 | Albert et al. |
| 5,576,952 A | * | 11/1996 | Stutman et al. ............ 600/300 |
| 5,735,285 A | | 4/1998 | Albert et al. |
| 6,097,308 A | | 8/2000 | Albert et al. |
| 6,198,394 B1 | * | 3/2001 | Jacobsen et al. ......... 340/573.1 |
| 6,221,012 B1 | | 4/2001 | Maschke et al. |
| 6,264,614 B1 | | 7/2001 | Albert et al. |
| 6,517,497 B1 | | 2/2003 | Rymut et al. |
| 6,985,078 B1 | * | 1/2006 | Suzuki et al. .......... 340/539.12 |
| 7,009,511 B1 | * | 3/2006 | Mazar et al. ............... 340/531 |
| 2003/0045279 A1 | | 3/2003 | Shostak |
| 2003/0120164 A1 | | 6/2003 | Nielsen et al. |

FOREIGN PATENT DOCUMENTS

WO    WO 03/021990 A1    3/2003

OTHER PUBLICATIONS

Vocera Communications System, Wearable Instant Voice Communication, 2003, Vocera Communications, Inc., Cupertino, CA, USA.
Mobile Pro 900 Handheld PC, 2003, NEC Solutions (America), Inc., Santa Clara, CA, USA.

(Continued)

*Primary Examiner*—Daryl C Pope
(74) *Attorney, Agent, or Firm*—Andrus, Sceales, Starke & Sawall

(57) ABSTRACT

A data acquisition system can include an acquisition device and a receiving device. The acquisition device includes inputs that receive data from sensors connected to a subject, a wireless and/or a wired transmitter that transmits data received by the inputs, and a housing carrying at least some of the components of the acquisition device. The housing may be wearable by a patient. The acquisition device may be switchable between a tethered data transmission mode and an untethered data transmission mode. The receiving device includes a receiver that receives data transmitted by the acquisition device, and may include an output that outputs data to a host. The system may be configured to transmit data from the data acquisition device to the local monitor point-to-point. The system is particularly useful for monitoring high acuity patients that may or may not require ambulation.

49 Claims, 14 Drawing Sheets

OTHER PUBLICATIONS

PPT 8800 Series With Windows, Mobile 2003 Software for Pocket PCs, 2002, pp. 1-4, Symbol Technologies, www.symbol.com/ppt8800.
MiniScan Series, Miniature, High-Performance Scan Modules, 2003, Symbol Technologies, Inc., www.symbol.com/oem.
PSM201, Bar Code Scanning Module for Motorola, IDEN Phones, 2003, Symbol Technologies, Inc., USA.
StatView Alarm Notification System, 2001, General Electric Company, USA.
StatView RespondNow, 2003, General Electric Company, USA.
StatView RespondNow, 2002, General Electric Company, USA.
IBM & Citizen Watch develop Linux-based "WatchPad", Oct. 11, 2001, pp. 1-4, DeviceForge LLC, LinuxDevices.com.
Overview, HP iPAQ Pocket PC h5500 Series, 2003, pp. 1-9, Hewlett-Packard Development Company, L.P., http:www.hp.com/go/iPAQ.
Hp iPAQ h4355 pocket pc (FA173A#ABA) 1994-2003, pp. 1-2, Hewlett-Packard Company, http://www.shopping.hp.com/cgi-bin/hpdirect/shopping/scripts/pro....
Biometrics In the real world, AuthenTec, Inc., pp. 1-2, Dec. 3, 2003, http://www.authentec.com/finalInteg/WhyTruePrint.htm.
AT&T Wireless, our biggest store: phones, Nokia 3300, 2003, pp. 1-3, AT&T Wireless, http://www.attwireless.com/personal/products/phonedetails.jhtml?i....
Aloysius Choong, HP's Biometric PDA, Dec. 10, 2002, pp. 1-3, CNET Networks, Inc., http://www.zdnet.com.au/reviews/coolgear/pda/story/0,20000235....
AT&T Wireless, our biggest store: phones, Sony Ericsson P800, 2003, pp. 1-3, AT&T Wireless, http://www.attwireless.com/personal/products/phonedetails.jhtml?i....
Microban Protection, Dec. 8, 2003, pp. 1-3, Microban Products Company, Huntersville, NC, http://www.ca-innovations.com/smartfeatures.asp?page=microban....
Plastic fabrics: Keeping prices down as material costs go up, Jul. 7, 2003, pp. 1-4, Trade Media Holdings Ltd, http://www.trimmings.globalsources.com/am/article_id/900000004....
Raised toilet seats, Dec. 8, 2003, pp. 1-3, Gordon Ellis & Co., UK.
Linux on a wrist watch, Nov. 1, 2001, p. 1 of 1, Linus Torvalds, http://www.research.ibm.co/WearableComputing/factsheet.html.
MWS antibacterial/anti-mold chain, 1997-2003, pp. 1-3, Tsubakimoto Chain Co, http://tsubakimoto.com/products/chain/conveyor_chain/mws_antib....
Universal Display Corporation, Product Concepts,Mar. 2001, p. 1 of 1, Universal Display Corporation, http://www.universaldisplay.com/concepts.php.
Universal Display Corporation, Technology, High Efficiency Materials, Mar. 2001, p. 1 of 1, Universal Display Corporation, http://www.universaldisplay.com/high.php.
Universal Display Corporation, Technology, SOLED Stacked Organic Light Emitting Device, Mar. 2001, pp. 1-2, Universal Display Corporation, http://www.universaldisplay.com/soled.php.
Universal Display Corporation, Technology, TOLED Transparent Organic Light Emitting Device, Mar. 2001, pp. 1-2, Universal Display Corporation, http://www.universaldisplay.com/toled.php.
Universal Display Corporation, Technology, FOLED Flexible Organic Light Emitting Device, Mar. 2001, pp. 1-2, Universal Display Corporation, http://www.universaldisplay.com/foled.php.
Universal Display Corporation, OLED Technology, Mar. 2001, pp. 1-2, Universal Display Corporation, http://www.universaldisplay.com/tech.php.
The Changing Display Industry: CRT and Flat Panel, Jan. 2002, pp. 1-12, Business Communications Co., http://www.mindbranch.com/catalog/product.jsp?code=R2-540.
Leslie Versweyveld, eMagin Supplies OLED Displays as 3D Imaging Source for VRmagic Surgical Training Simulator, Sep. 24, 2003, pp. 1-4, http://www.hoise.com/vmw/03/articles/vmw/LV-VM-10-03-26.html.
BlackBerry 7280 Wireless Handheld, Dec. 3, 2003, p. 1 of 1, http://www.blackberry.net/products/blackberry7200/blackberry728....
RIM 950 Wireless Handheld, Dec. 3, 2003, 2003, Research In Motion Limited, http://www.blackberry.net/products/handhelds/rim950.shtml.
Blackberry 5810 Wireless Handheld, 2003, p. 1 of 1, Research In Motion Limited, http://www.blackberry.net/products/blackberry5810/index.shtml.
RIM 850 Wireless Handheld and RIM 950 Wireless Handheld, 2003, p. 1 of 1, Research In Motion Limited, http://www.blackberry.net/products/rim850_950/index.shtml.
AuthenTec, Inc., Fingerprint Sensors using TruePrint, Technology for Convenient Security, 2003, p. 1 of 1, AuthenTec, Inc., http://www.authentec.com.
2002 BiometriTech Product Of The Year Winners, 1997-2003, pp. 1-10, Technology Marketing Corporation, Norwalk, CT, http://www.biometritech.com/features/poty03.htm.

* cited by examiner

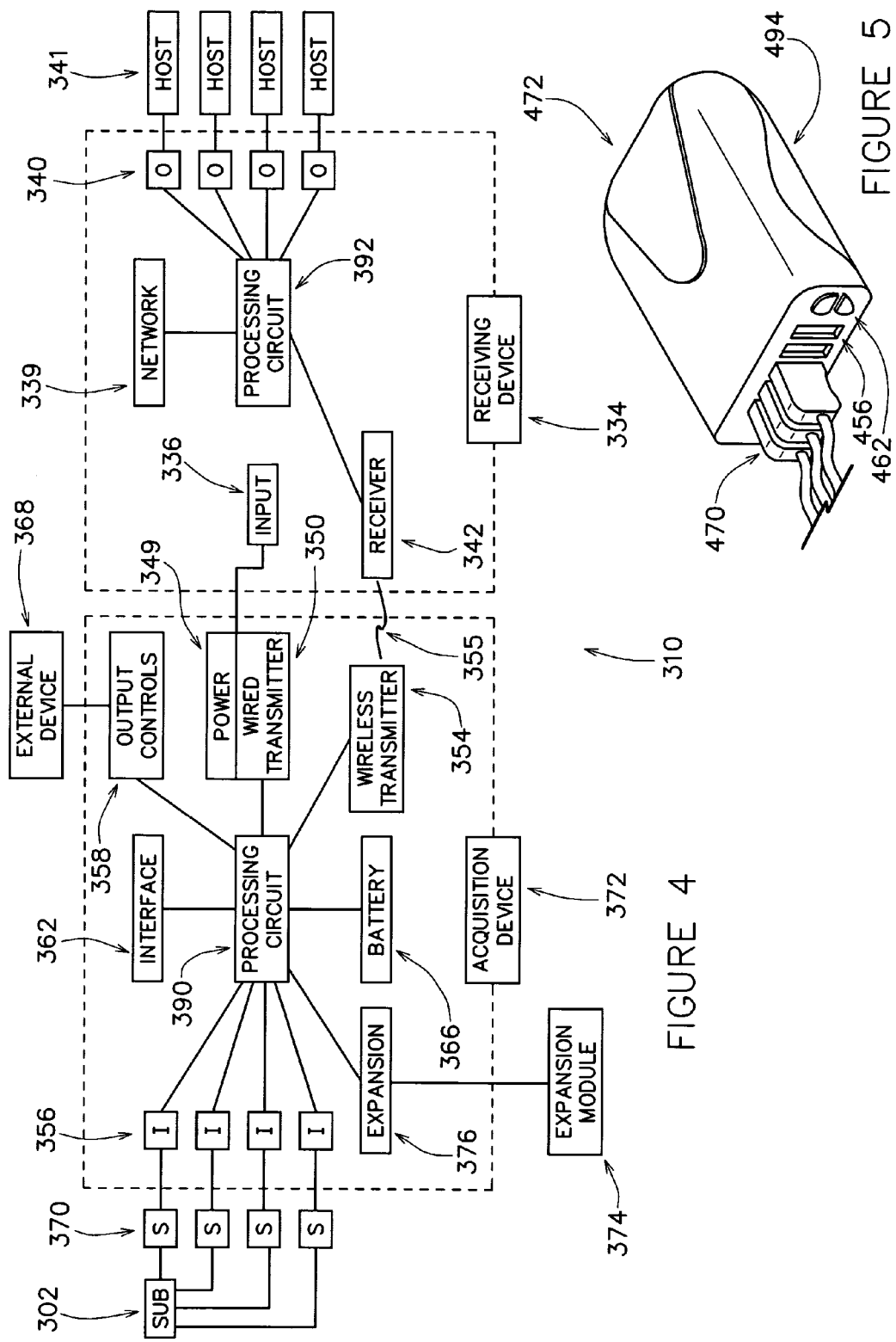

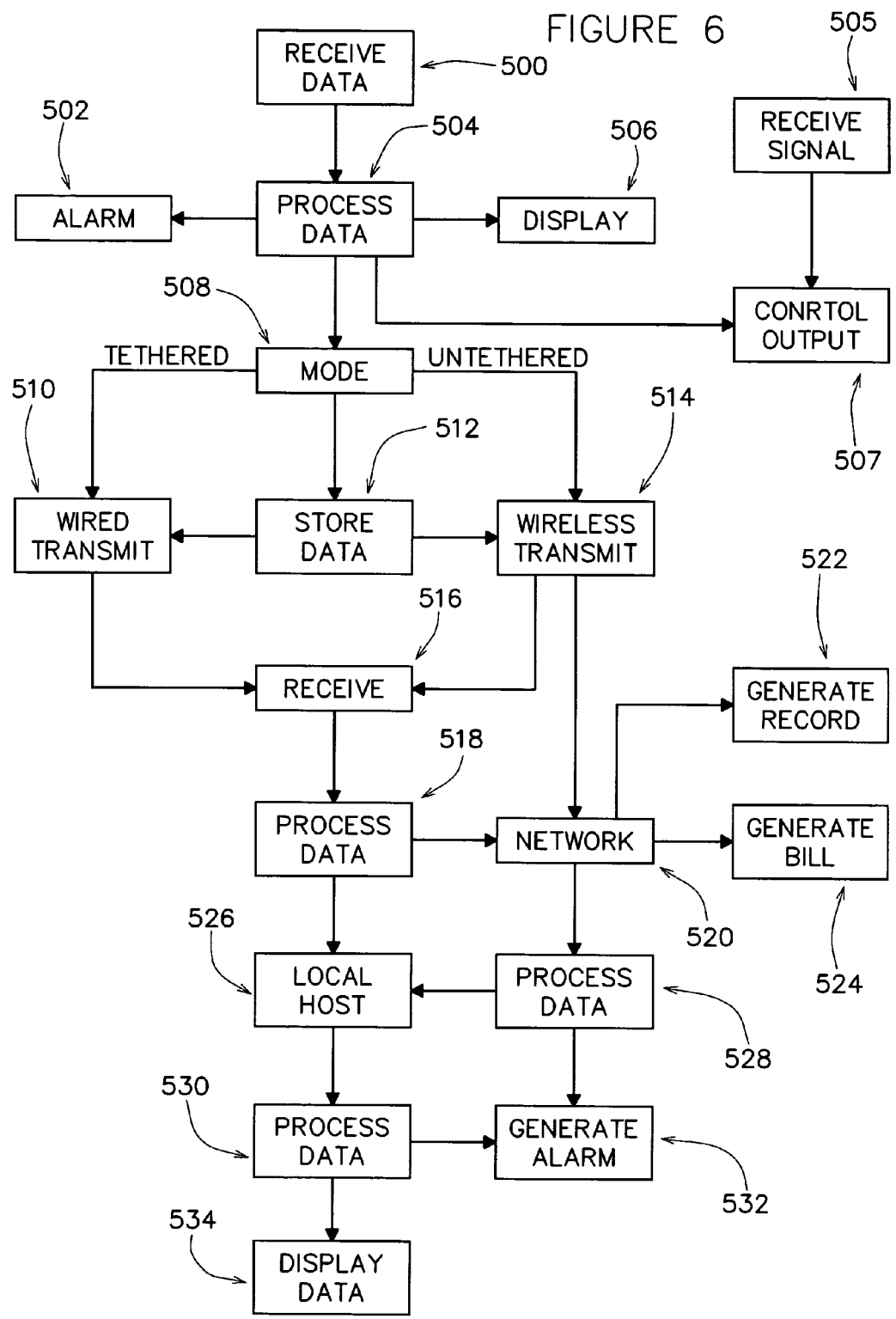

WIRELESS SUBJECT MONITORING SYSTEM

BACKGROUND

Patient mobility is an integral part of many patient care regimens in high acuity care environments. As part of the recovery process, patients are encouraged to periodically stand up, make short trips to the window, the bathroom, and other patient mobility events. Lack of patient mobility can result in physiologic complications such as deep vein thrombosis, infection, and overall prolonged recovery periods. Although it is preferable to provide continuous monitoring during these patient mobility events, it is often too difficult. Patient cables are often too short to allow for optimal range of patient movement, yet long enough to provide a tangle hazard to the patient and to the caregiver. As a result, the patient is typically disconnected from the local/bedside monitoring device. Disconnecting the patient can be time consuming, results in an unmonitored patient, and creates a gap in the patient record. It would be preferable to have a system that allows for easy connection and disconnection of a patient from a local monitor. Also, it would be preferable to allow a patient to continue to be monitored while not physically connected to a local/bedside monitor such that a patient may be monitored during patient mobility events.

Patients who are classified as high acuity often have a number of different sensors, probes, and electrodes monitoring their condition at any one time. Further, high acuity patients should be closely monitored on a continual basis. It would be preferable to have a monitoring system that allows high acuity patients to be able to move around while being monitored.

Patient mobility events for many patients do not involve leaving the vicinity of the local/bedside monitor, such as walking around a room or going to the bathroom. Further, if a patient is having problems it would be desirable to know this as soon as possible. Further still, when multiple connections and data transfers must take place for data to go from the sensor to the monitor, the chance that data will be degraded or will be unable to be transferred increases. It would be desirable to have a monitoring system that transfers data with as few connections as possible, especially when monitoring high acuity patients.

While wireless data transmission can offer the advantage of substantially continuous monitoring, it is not as reliable as a direct connection. Other objects may emit fields or signals that interfere with the ability of a wireless transmitter to accurately transmit data. For instance, in an operating room environment where electrocautery equipment is being used, the electrocautery equipment may emit fields that can interfere with wireless data transmission. It would be preferable to have a system that could combine the portability of wireless data transmission with the reliability of wired data transmission. Further, it would be desirable if the system were easier to operate than unplugging the sensors from one device and then replugging the sensors into a second device.

The teachings hereinbelow extend to those embodiments which fall within the scope of the appended claims, regardless of whether they accomplish one or more of the above-mentioned needs.

SUMMARY

One embodiment relates to a monitoring system having an acquisition device and a receiving device. The acquisition device includes an input that is configured to receive data from at least one sensor coupled to a subject, and a wireless transmitter that continuously transmits data received by the input. The receiving device includes a receiver that receives data transmitted by the acquisition device, and an output that outputs data to at least one host. The system transmits data from the data acquisition device to the local host point-to-point.

Another embodiment is directed to an acquisition device for use with multi-parameter subjects. The acquisition device includes a plurality of inputs that are configured to receive data from a plurality of sensors coupled to the subject, and a wireless transmitter that transmits data received by the inputs. The acquisition device is particularly suitable for monitoring parameters typically associated with high acuity patients.

Another embodiment provides an acquisition device for use with high acuity patients. The acquisition device includes an input that receives data from an invasive sensor coupled to a patient, and a wireless transmitter that transmits data received by the inputs.

Another embodiment relates to an acquisition device. The acquisition device includes an input that receives data from at least one sensor coupled to a subject, a wired transmitter that transmits data received by the input in a tethered data transmission mode, a wireless transmitter that transmits data received by the input in an untethered data transmission mode, and a data transmission mode, the data transition mode being switchable between the tethered data transmission mode and the untethered data transmission mode.

Another embodiment is directed to a data acquisition system for use with high acuity patients. The data acquisition system can include an acquisition device and a receiving device. The acquisition device includes a plurality of inputs that are configured to receive data from a plurality of sensors coupled to a patient, a wired transmitter that transmits data received by the inputs in a tethered data transmission mode, a wireless transmitter that transmits data received by the inputs in a wireless data transmission mode, a housing carrying at least some of the components of the acquisition device, the housing configured to be portable by a patient, and a data transmission mode, the data transition mode being switchable between the tethered data transmission mode and the untethered data transmission mode. The receiving device includes a receiver that receives data transmitted by the acquisition device, and an output that outputs data to at least one local host. The system transmits data from the data acquisition device to the local host point-to-point.

Another embodiment provides a method for monitoring a subject. The method includes receiving data relating to high acuity parameters from sensors coupled to the subject; and continuously transmitting the data to a local host point-to-point.

Other principle features and advantages of the invention will become apparent to those skilled in the art upon review of the following drawings, the detailed description, and the appended claims.

BRIEF DESCRIPTION OF THE DRAWINGS

FIG. 4 is a schematic diagram of a monitoring system according to another embodiment of the invention;

FIG. 5 is a diagram of an acquisition module according to one embodiment of the invention; and FIG. 6 is a flow chart of steps that could be performed by a monitoring system according to any of the preceding embodiments or another embodiment of the invention.

DETAILED DESCRIPTION OF THE EXEMPLARY EMBODIMENTS

Figure 1A:
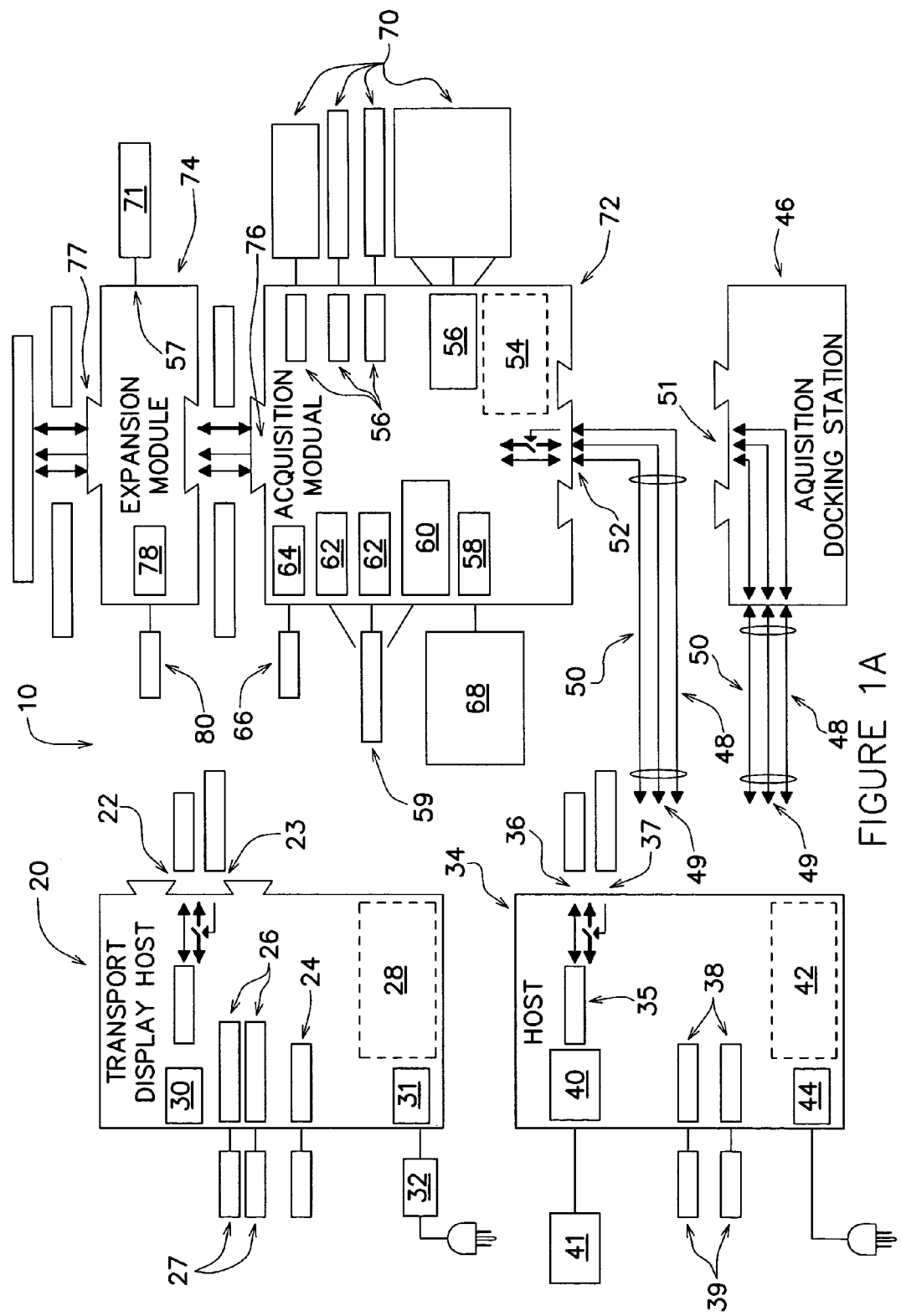
FIGS. 1A–F are schematic diagrams of a monitoring system according to one embodiment of the invention.
Figure 1B:
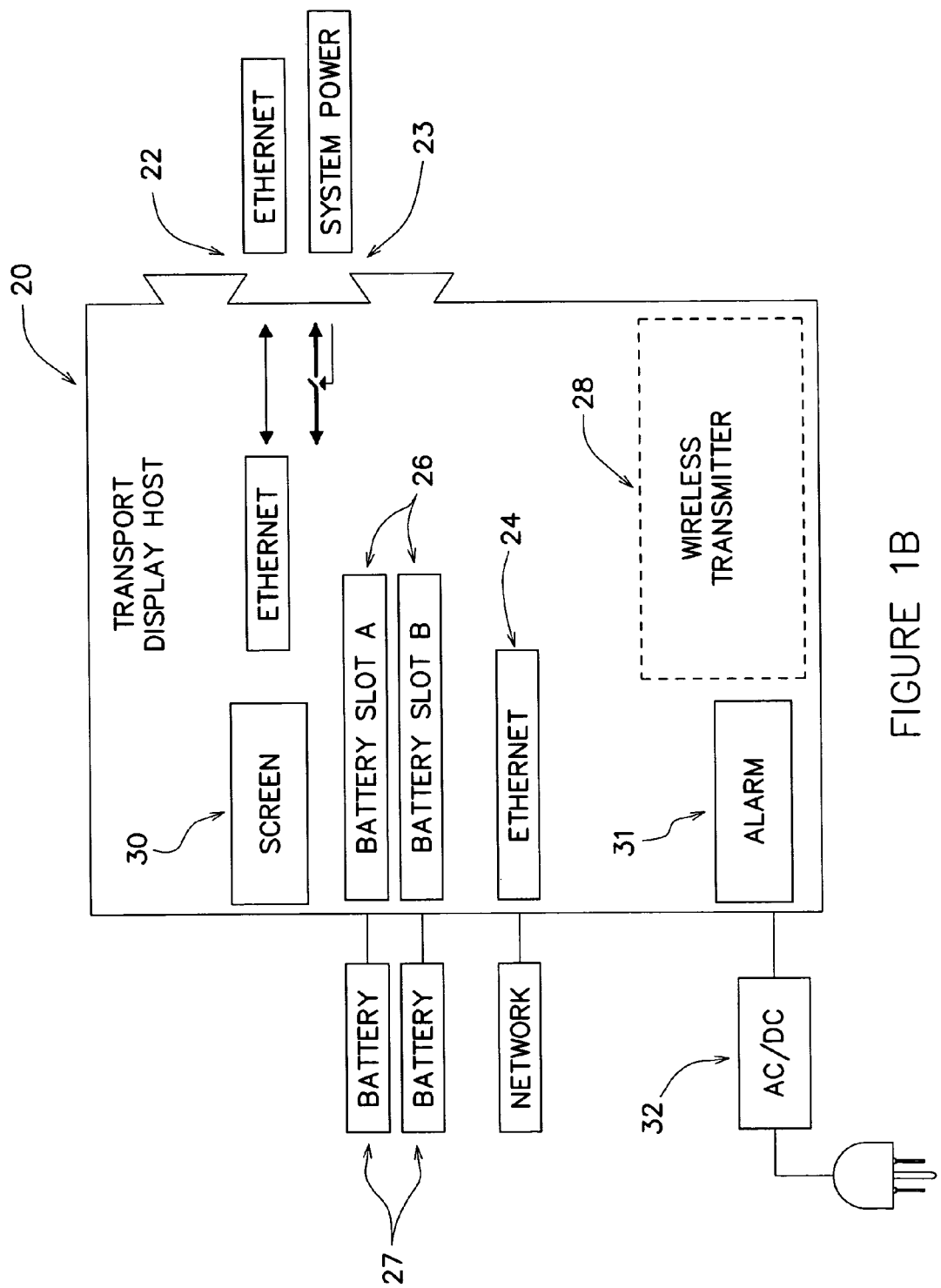
Figure 1C:
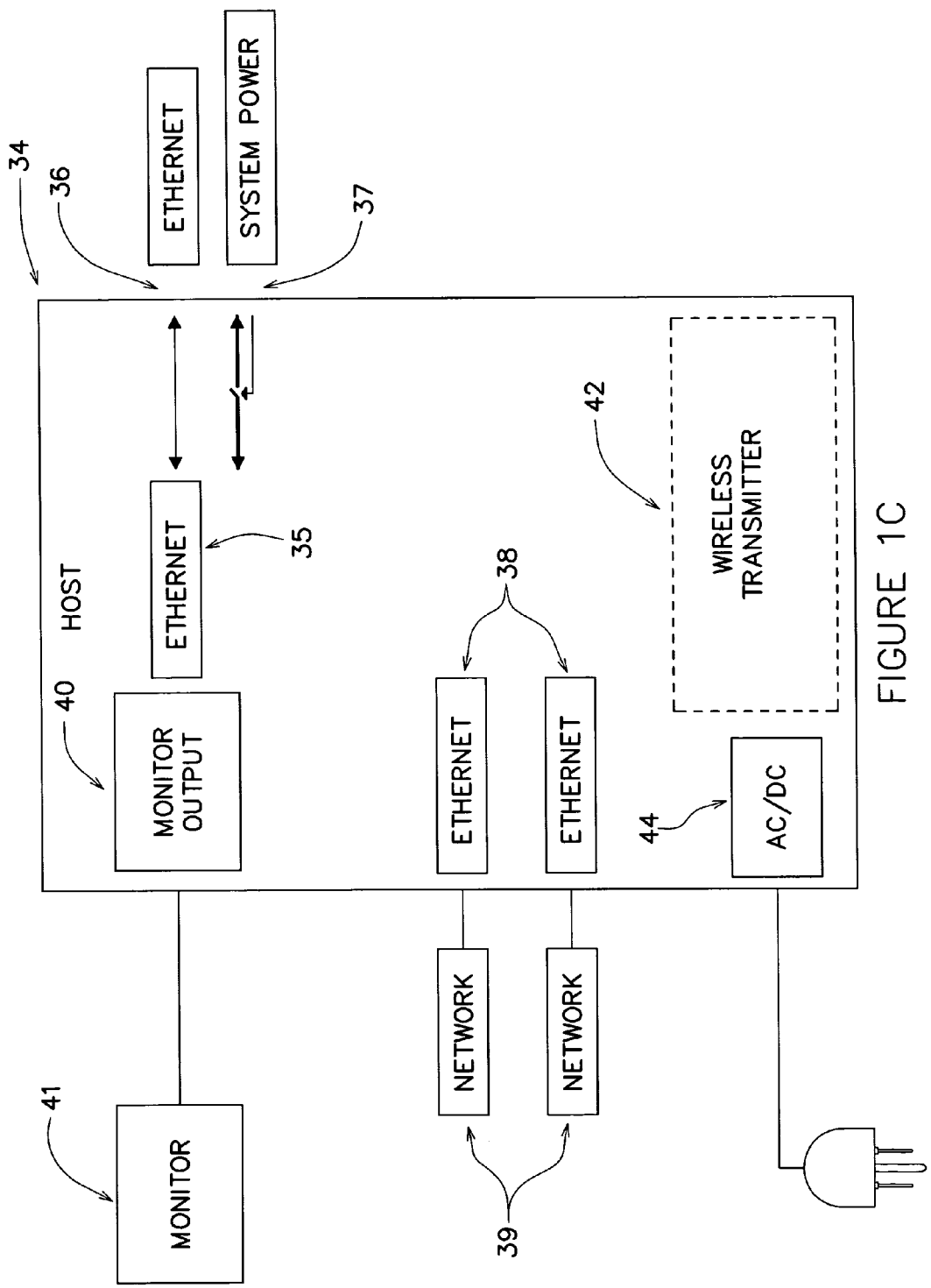
Figure 1D:
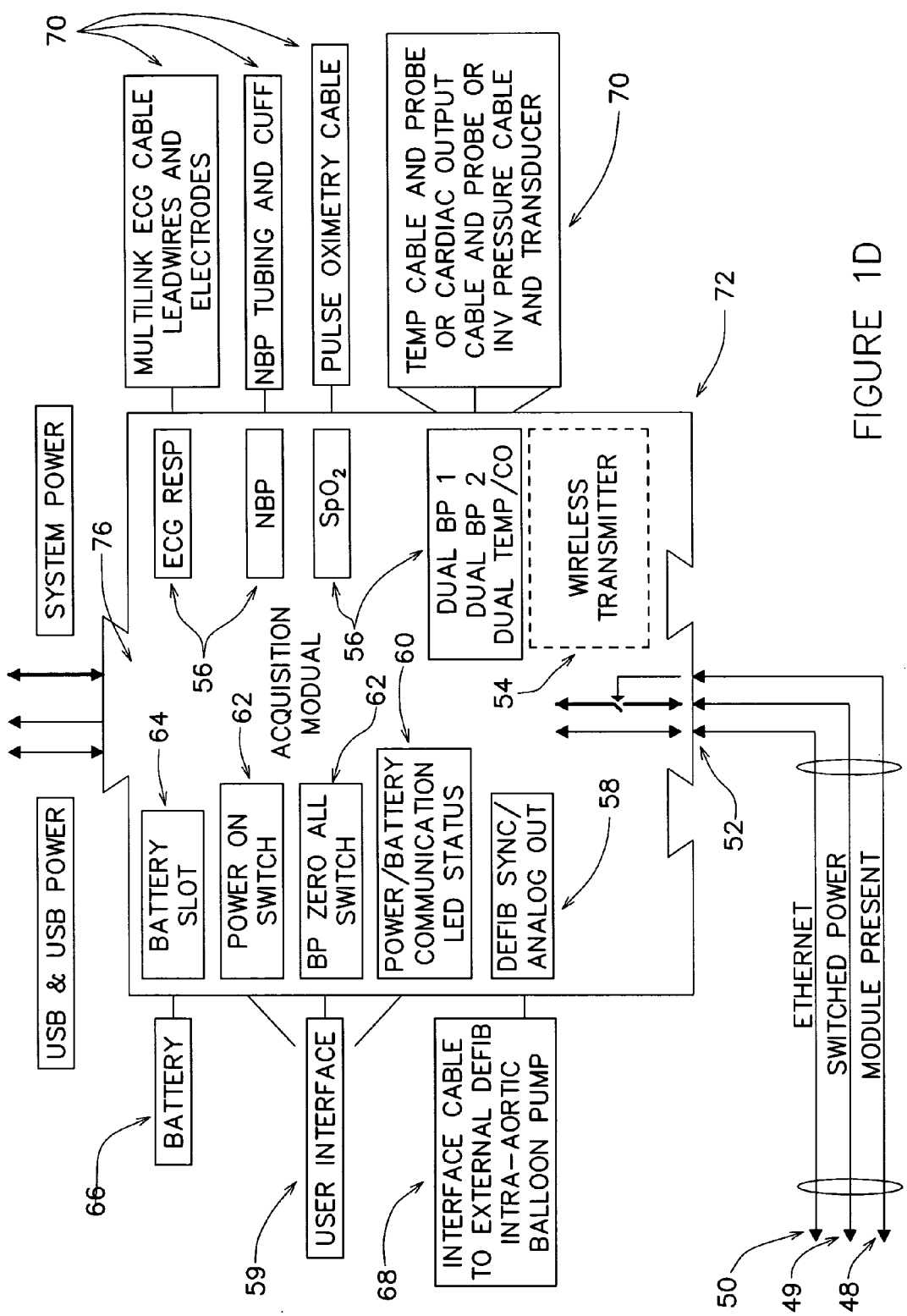
Figure 1E:
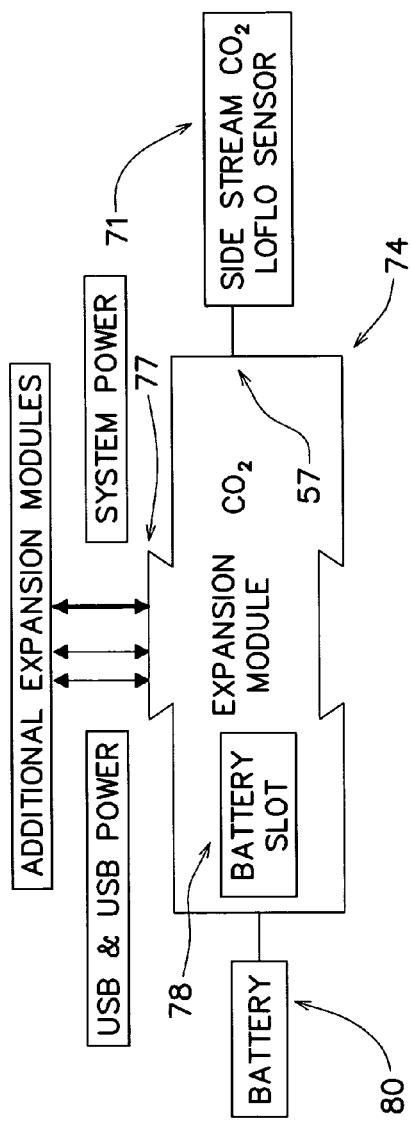
Figure 1F:
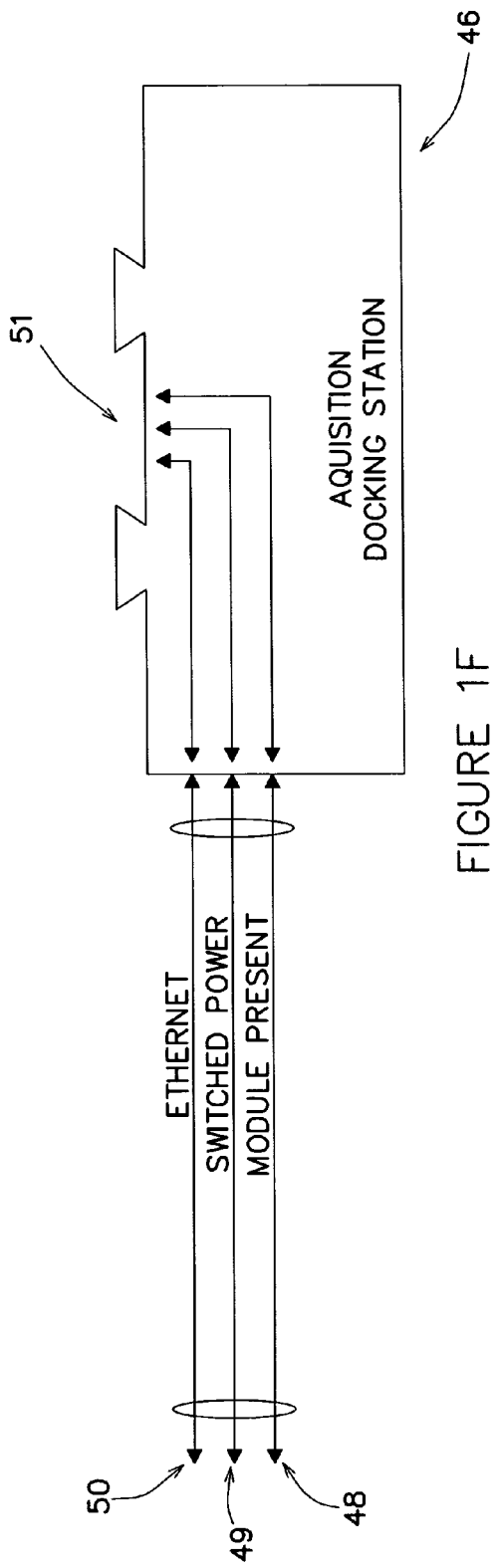

Referring to FIGS. 1A–F, a monitoring system 10, may include a data acquisition module 72, a host 34 or a transport host 20, a docking station 46, and/or an expansion module 74. Acquisition module 72 receives data from sensors 70 and transfers the data to a local host 20,34. Data may be transferred from acquisition module 72 to host 20,34 using a wired or a wireless connection. If a wired connection is used, a docking station 46 may be used to facilitate the connection. Acquisition module 72 may receive further data from an expansion module 74 which may contain additional sensors.

Acquisition module 72 includes inputs 56 which are configured to receive data from sensors 70 coupled to a subject, such as a patient. Some examples of patient sensors that can be used include electrocardiograph (ECG) electrodes, non-invasive blood pressure (NBP) cuffs, pulse oximetry probes, temperature probes, cardiac output probes, and invasive blood pressure transducers. Inputs 56 may be configured to recognize the type and/or manufacturer of the sensor coupled to input 56. This may be done using mechanical linkages, electronic linkages, wireless connections, 1-wire technology, or some other technology used to identify a subject. If 1-wire technology is used, data relating to the sensor being used (such as duration of usage, calibration values, etc.) can be transmitted from the sensor and/or to the sensor.

Acquisition module 72 may also include a user interface 59. User interface 59 may include user inputs 62 and a display 60. User inputs 62 may include calibration inputs, a power switch, a data transmission mode switch, and inputs for other information or commands. Display 60 may include LEDs, an LCD screen, or other forms of display. Display 60 may display information such as power/battery status, data transmission mode, monitoring results, etc.

Acquisition module 72 may also be configured to include output controls 58 for control devices 68 coupled to a subject. Some examples of medical devices which may be coupled to a subject include external defibrillators, intra-aortic balloon pump, neonatal ventilator, and/or any other controlled medical device.

Acquisition module 72 further includes a battery 66. Battery 66 may be a rechargeable battery, and/or may be removable. If battery 66 is removable, acquisition module 72 may include a battery slot 64 for facilitating the exchange of battery 66.

Acquisition module 72 may also include an expansion port 76 that allows expansion modules 74 to be added to acquisition module 72. Expansion modules 74 may include additional sensor inputs 57, additional batteries 80 for additional power, additional output controls, additional user interfaces, additional communication devices, or other components that expand the functions of data acquisition module 72. Expansion modules 74 may have their own processing circuits, or may transfer data to be processed by acquisition module 72. Expansion modules 74 may further include additional expansion ports 77 for additional expansion modules. Expansion port 76 may include a universal serial bus (USB) connection, and may be configured to transfer data and/or power to or from expansion module 74. Reference to "an acquisition device" includes, unless stated otherwise, either an acquisition device by itself or an acquisition device coupled to one or more expansion modules.

Acquisition module 72 is configured to transmit data to hosts 20,34 in a wired data transmission mode and in a wireless data transmission mode. Wireless transmitter 54 can be used to transmit data wirelessly to hosts 20,34. Alternatively, wired data port 52 can be used to transmit data over a wired connection to hosts 20,34.

Wireless transmitter 54 preferably transfers data point-to-point to host 34. Point-to point data transfer indicates that data is transferred directly from the acquisition module 72 to host 34 where host 34 is located in the vicinity of acquisition module 72. Transferring data point-to-point is generally meant as not being transferred from an acquisition module 72 to a network 39 and then to host 34. This is not to say that host 34 may not have a device connected to host 34 which facilitates wireless transfer of data to host 34. Wireless transmitter 54 may also be configured to transmit data to hosts 20,34 over a network 39. For example, wireless transmitter 54 may be configured to transmit data point-to-point when hosts 20,34 are in range and to transmit data over a network 39 when hosts 20,34 are not within range.

Acquisition module 72 may also be configured to transmit data using wired data port 52. Wired data port 52 may include a data transmission portion 50 for transmitting data. Data transmission portion 50 may use any number of technologies such as serial data transmission, Ethernet data transmission, etc. Wired data port 52 may also include a power input portion 49 such that acquisition module 72 can be powered by an external power source and/or such that battery 66 may be recharged by an external power source. Power input portion 49 and data transmission portion 50 are preferably configured to be a single input such that connecting one wire to wired data port 52 can facilitate both data transmission and powering of acquisition module 72. This may be facilitated by using a universal serial bus (USB) port, powered Ethernet, or some other technology.

Wired data port 52 may also include a module detection portion 48 that determines whether a wired connection is being made. Module detection portion 48 can determine whether a wired data connection is being made. Data can then automatically be routed to wireless transmitter 54 or wired data port 52 based on whether a wired connection is being made.

Wired data transfer may be facilitated by docking station 46. Docking station 46 may connect to acquisition module 72 through wired data port 52 or through a separate data port. Docking station 46 connects to acquisition module 72 from acquisition module connection port 51. Docking station 46 can then be directly connected to host 34. Docking station 46 preferably has a data transmission portion 50, a power input portion 49, and a module detection portion 48. Docking station 46 may be a separate device, or may be integrated into a host device.

Host/receiving device 34 receives information from acquisition module 72 at input 36. Input 36 may include a wired receiver (such as an Ethernet card 35 and a power portion 37 that transfers power to acquisition module 72 when acquisition module is wired to host 34. Host 34 also has a wireless receiver 42 for receiving data transmitted wirelessly from acquisition module 72.

Host 34 further includes network interfaces 38 for connecting to one or more networks 39. Network interfaces 38 can be configured to allow a wired connection to networks 39 (such as Ethernet ports), or may facilitate wireless access to networks 39.

Host 34 also includes an internal power connection 44 to provide power to host 34. Power connection 44 may also be used to provide power to acquisition module 72 through power portions 37 and 49.

Host 34 also has a display output 40 that connects host 34 to a local/bedside display 41. Display 41 can then display information processed by acquisition device 72, host 34, and/or display 41. Display 41 may also be used to generate local alarms (alarms that are triggered in the vicinity of host 34).

Transport host/receiving device 20 is configured to be more easily transported. Transport host 20 includes external power connection 32 that can be connected to transport host 20 to provide power from a power outlet. External power connection 32 may also be used to recharge batteries 27.

Host 20 includes a screen 30 that can display information processed by host 20 and/or acquisition device 72. Host 20 also includes an alarm device that can trigger local alarms or remote alarms (alarms not necessarily occurring in the vicinity of host 20, such as an alarm at a nurse station, on a pager, on a personal digital assistant carried by a clinician, etc.).

Figure 2A:
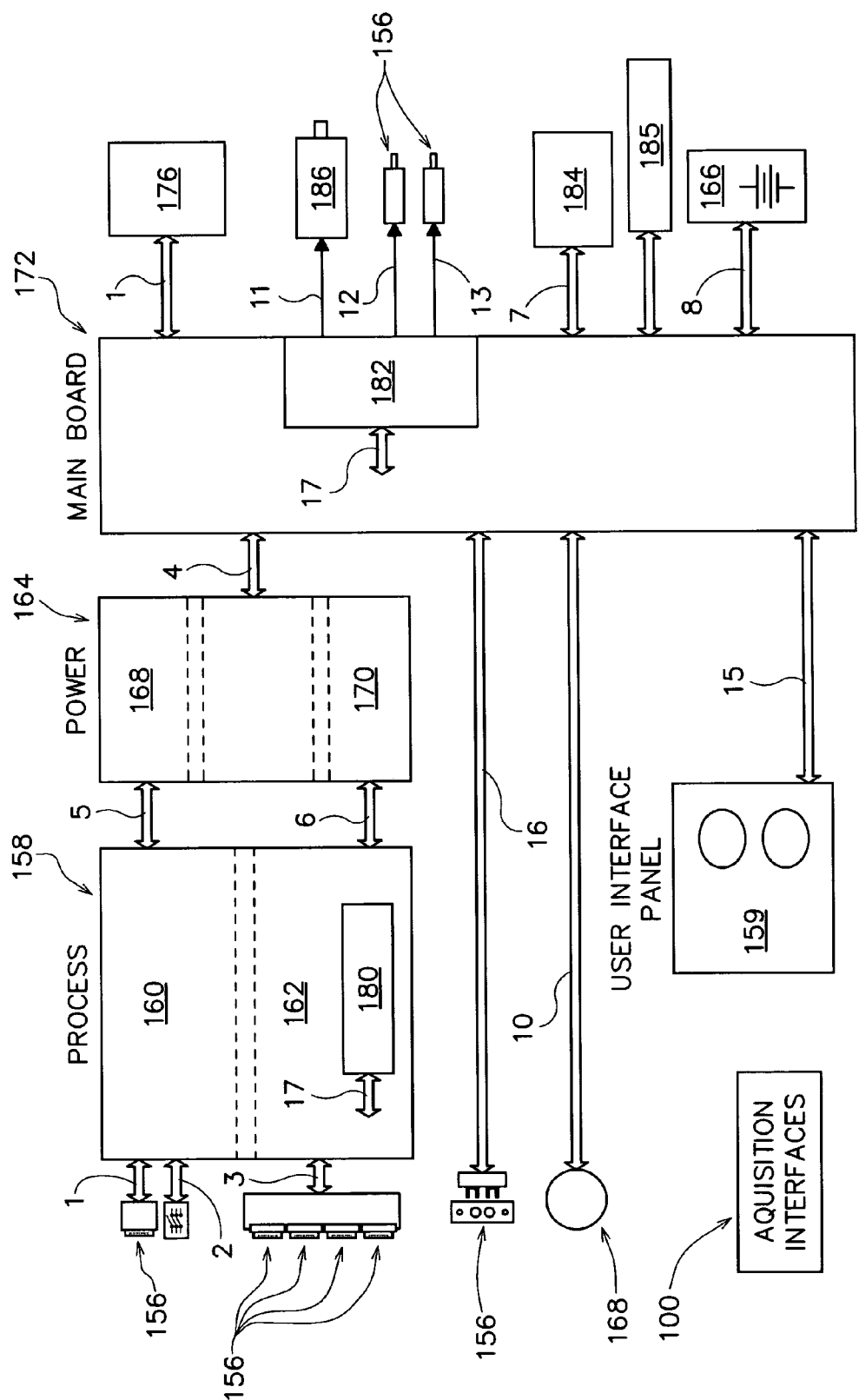
FIGS. 2A–C are schematic hardware diagrams of an acquisition module according to the embodiment of FIG. 1A.
Figure 2B:
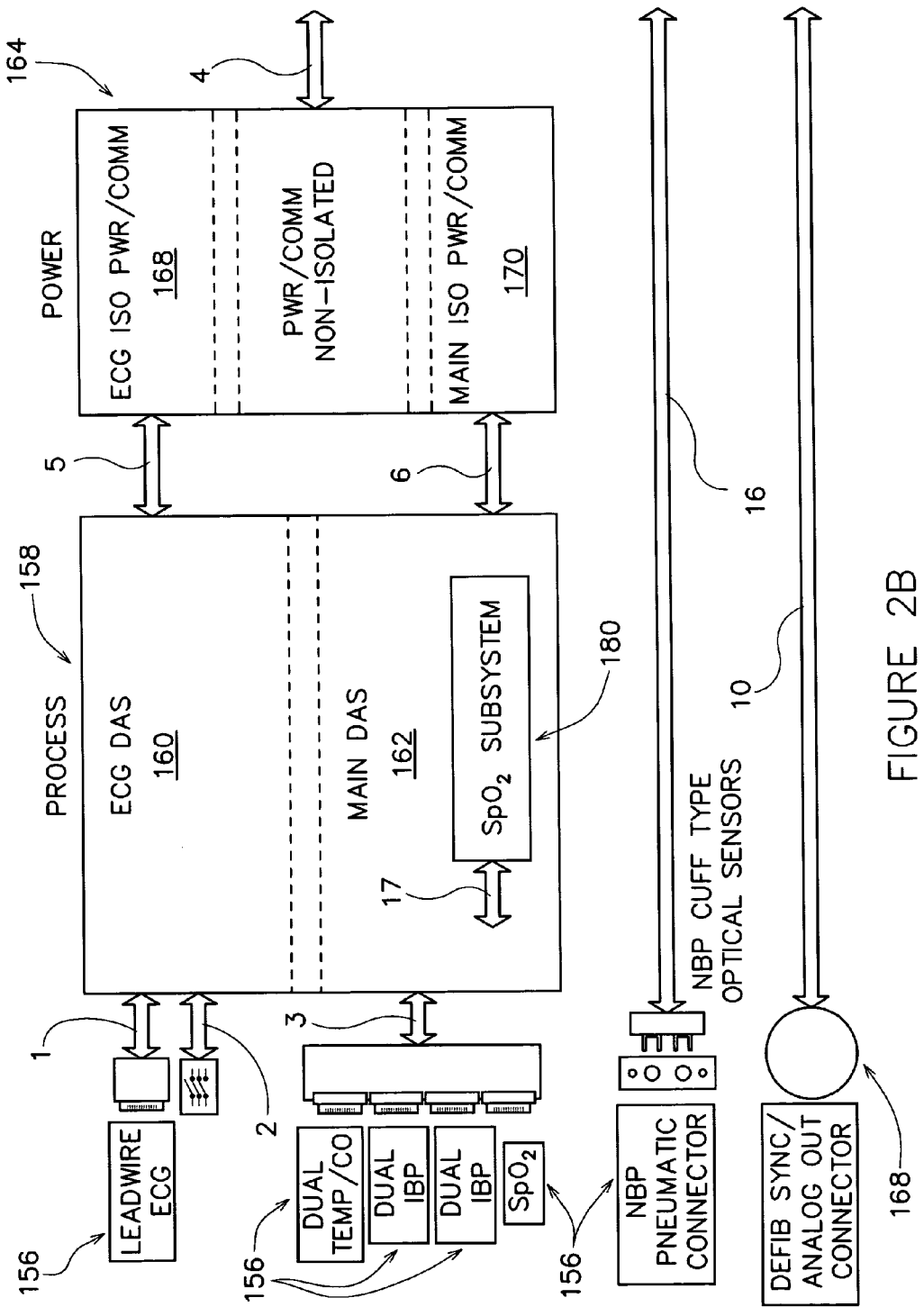
Figure 2C:
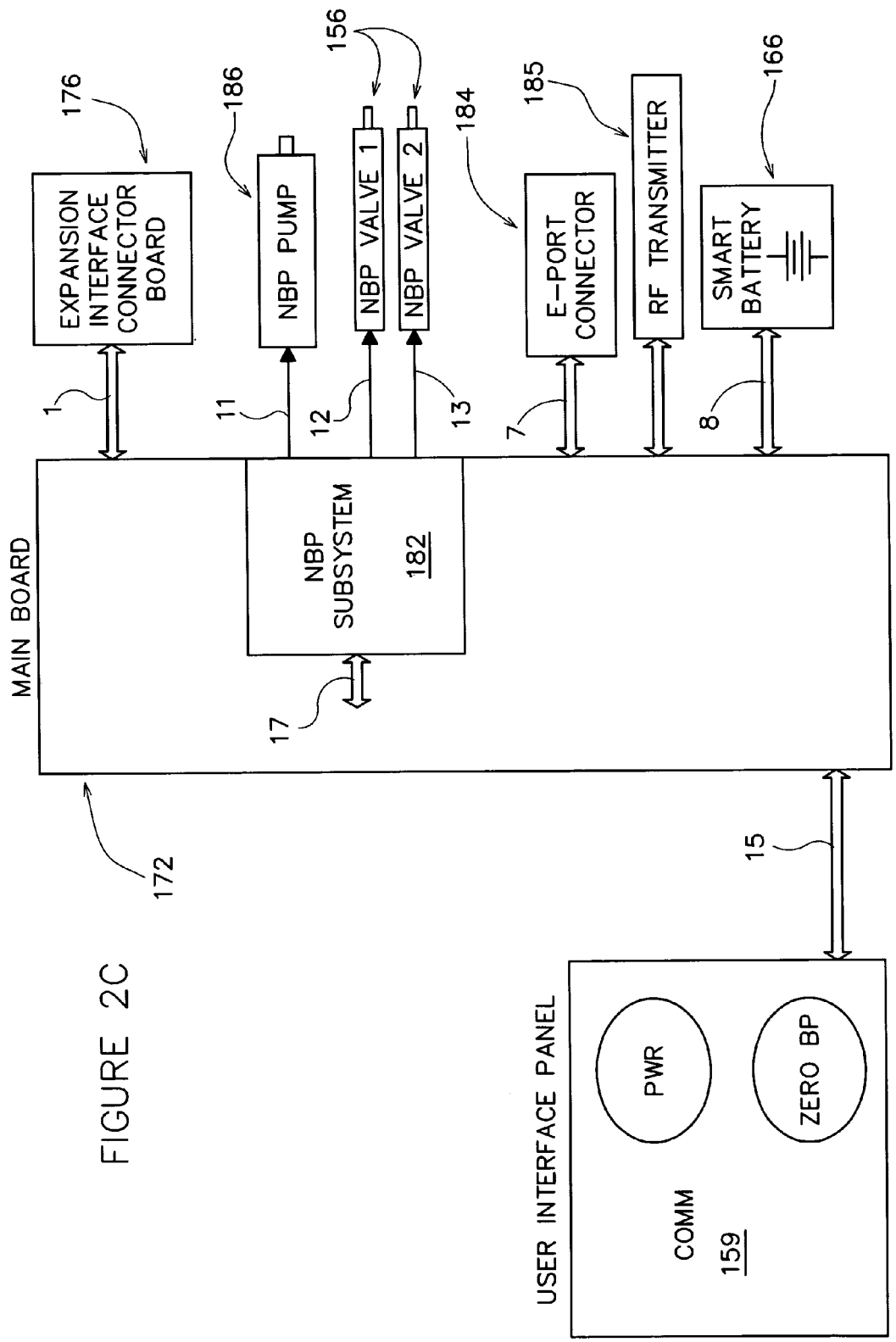
Figure 3A:
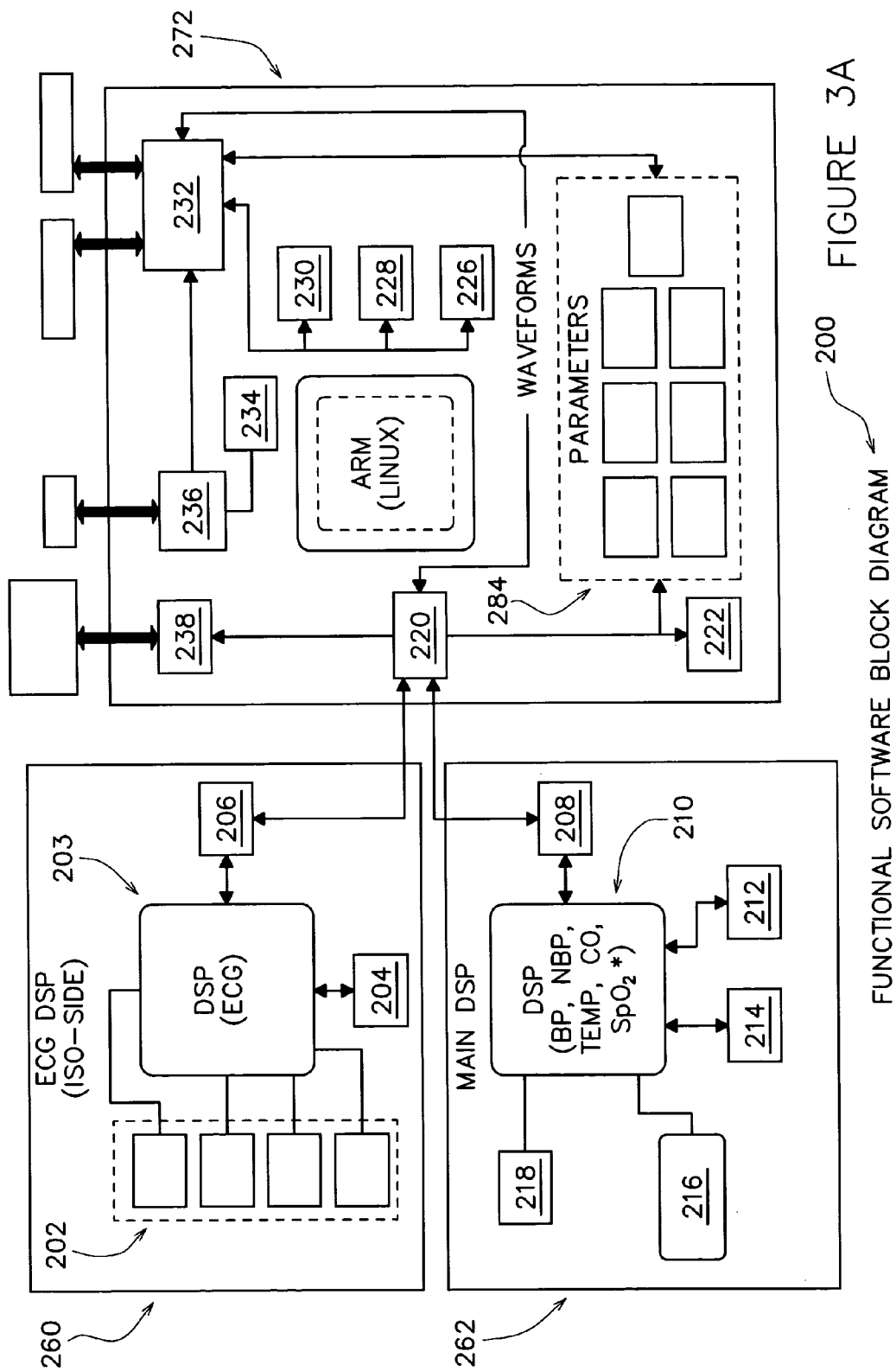
FIGS. 3A–D are functional software block diagrams of an acquisition module according to the embodiment shown in FIG. 2A.
Figure 3B:
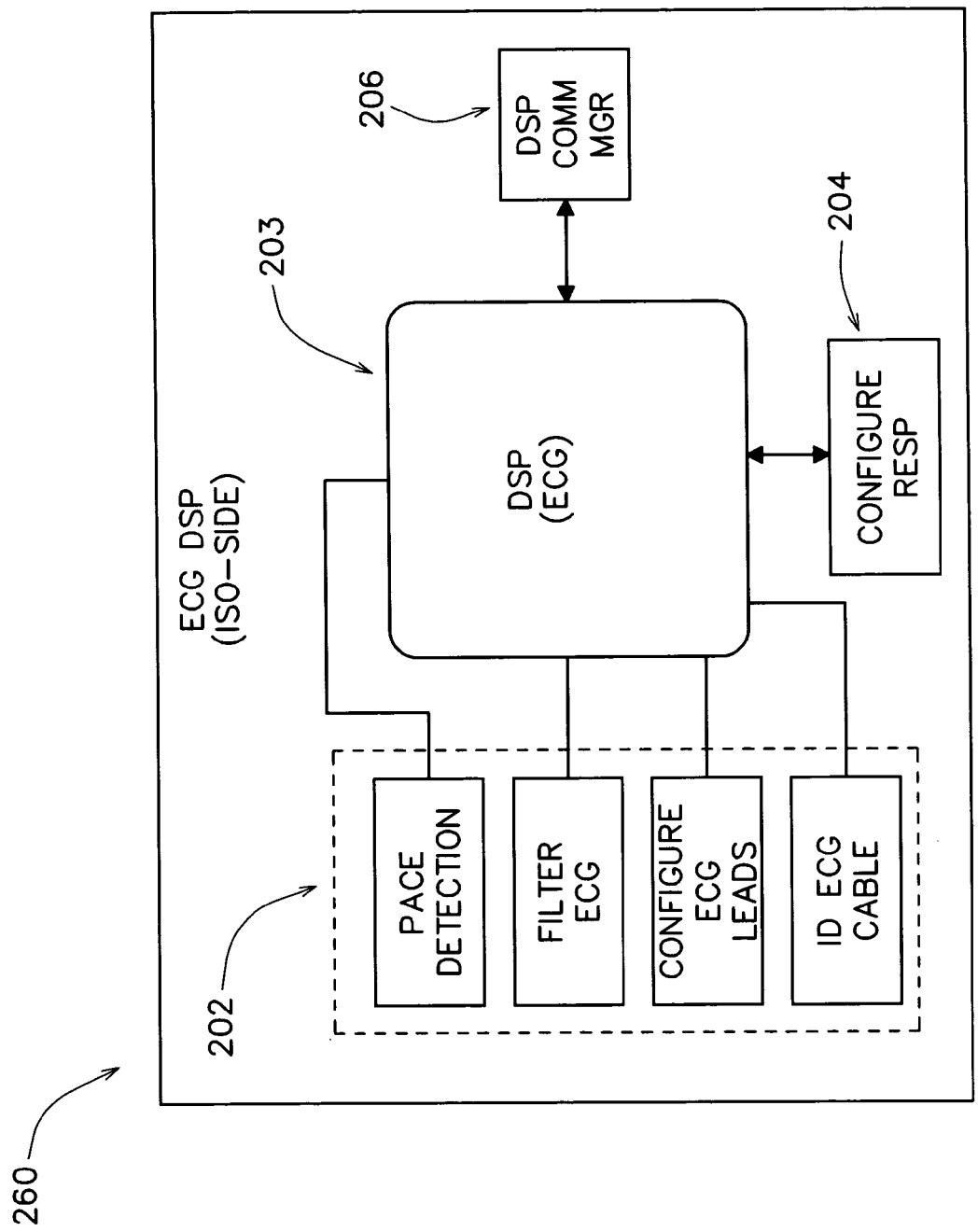
Figure 3C:
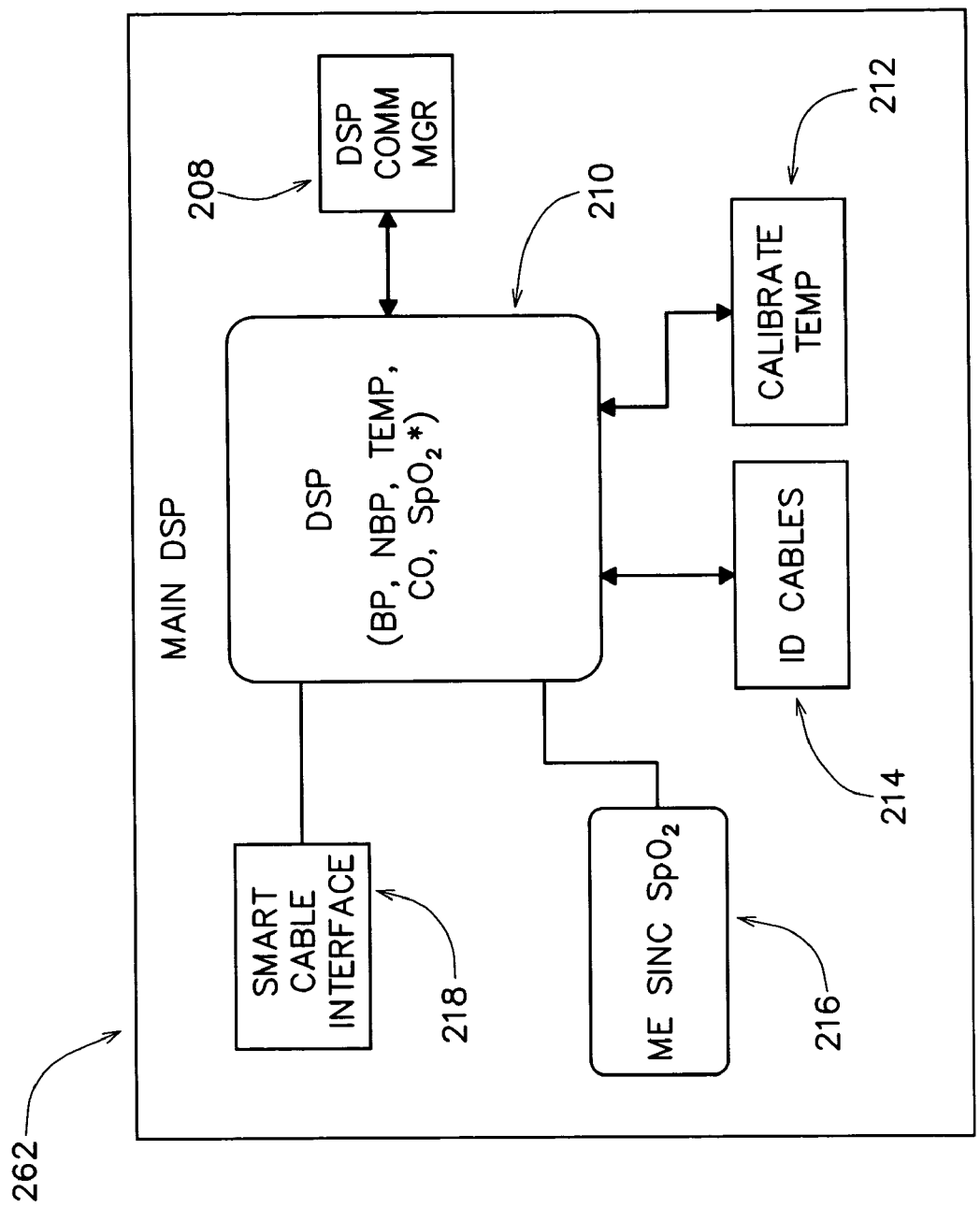
Figure 3D:
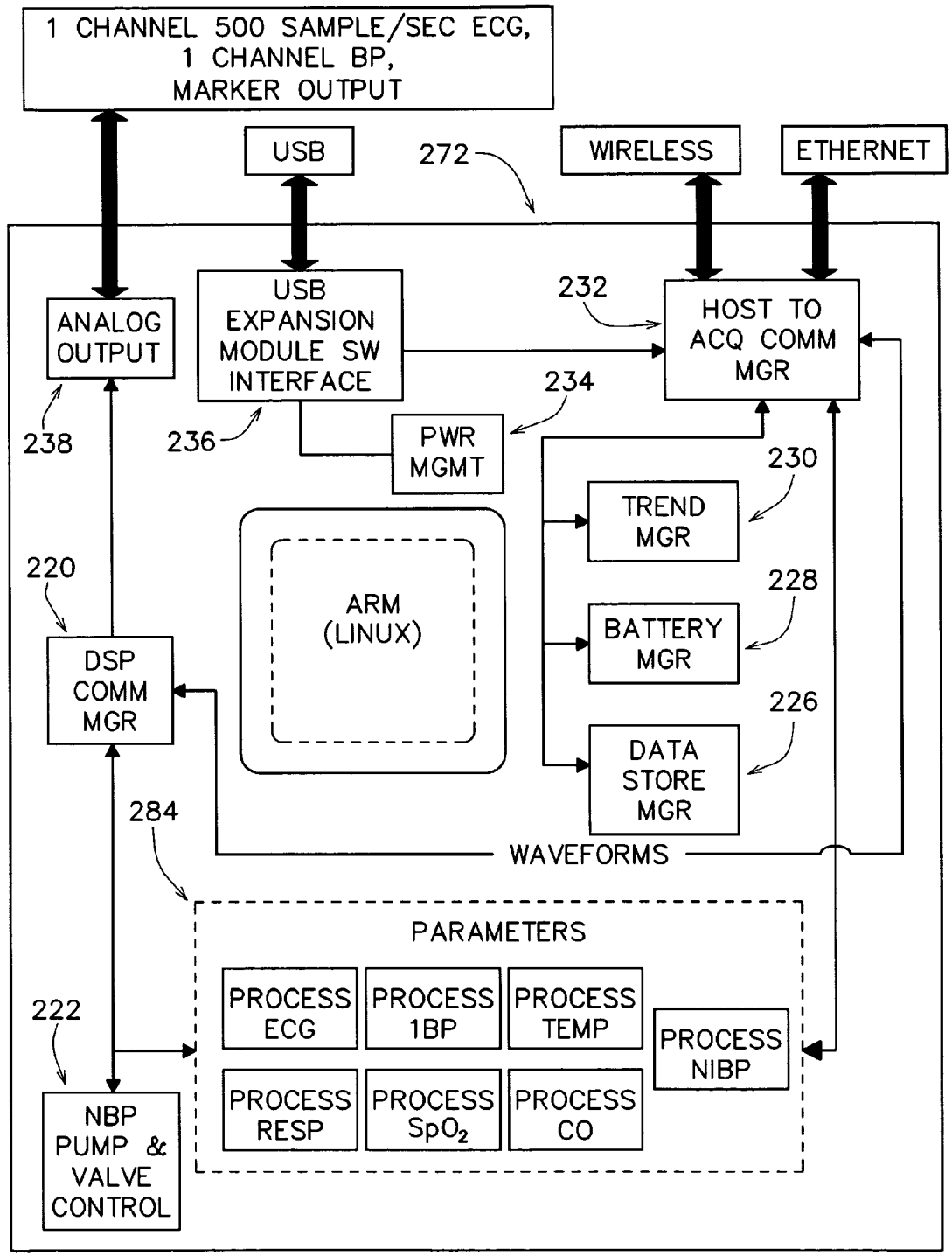

Referring to FIGS. 2A–C, hardware included in an acquisition interface 100 of acquisition module 72 includes inputs 156 that are configured to receive cabling from sensors 70 to facilitate transfer of data from sensors 70. Acquisition module 72 further includes smart battery 166 which provides power for acquisition module 72 when transmitting in a wireless data transmission mode, and which recharges when transmitting data in a powered, wired data transmission mode. Acquisition module 72 also includes expansion module interface board 176 for facilitating a data connection to an expansion module 74. Acquisition module 72 also includes user interface panel 159 which includes user inputs 62 and display 60.

Inputs 156 are connected to signal processing board 158. Signal processing board 158 includes a main processing board 162 that receives inputs from temperature sensors, cardiac output sensors, invasive blood pressure sensors, and pulse oximetry sensors, and an ECG processing board 160 that receives data from ECG electrodes.

Acquisition interface 100 also includes power board 164 and mainboard 172. Main board 172 connects to power board 164, expansion interface board 176, smart battery 166, Ethernet connector 184, wireless transmitter connector, non-invasive blood pressure (NBP) subsystem 182 (including pump 186), user interface panel 159, and output control board 168.

Referring to FIGS. 3A–D, acquisition software 200 includes main signal processing section 262 running on main processing board 162, ECG processing section 260 running on ECG processing board 160, and mainboard section 272 running on mainboard 172.

Main signal processing section 262 includes modules that control calibration of temperature sensors 212, that identify the type and/or function of the cables 212, that interface with the cables 218, and that process 210 the signals input on the main processing board. Main signal processing section 262 also includes a communication section 208 that facilitates communication with mainboard section 272.

ECG signal processing section 260 includes modules that control ECG functions 202, that configure respiration functions 204, and that perform other ECG signal processing operations 202. ECG processing section 262 also includes a communication section 206 that facilitates communication with mainboard section 272.

Mainboard section 272 runs a Linux operating system on an ARM processor. Mainboard section 272 includes a communication manager module 220 that facilitates communication between host manager 232, data processing modules 224, NBP manager, output control manager 213, main signal processing section 262, and ECG signal processing section 260.

Mainboard section 272 also includes trend manager module 230 and data storage manager module 226 which facilitate storage of data in the event that data cannot be successfully transmitted to a host. Mainboard section also includes a battery manager module that manages the use and charging of smart battery 166.

Mainboard section 272 further includes an expansion port module 236 that facilitates communication between an expansion module 74 and acquisition module 72.

Referring to FIG. 4, a monitoring system 310 includes an acquisition device 372 and a receiving device 334. Acquisition device 372 includes a plurality of inputs 356 that receive data from a plurality of sensors 370 coupled to subject 302. Data from inputs 356 is transferred to processing circuit 390. Processing circuit 390 can include various types of processing circuitry, digital and/or analog, and may include a microprocessor, microcontroller, application-specific integrated circuit (ASIC), or other circuitry configured to perform various input/output, control, analysis, and other functions to be described herein. Processing circuit 390 can digitize the data, can filter the data, can analyze the data, can combine the data, and/or can process the data in some other manner. Processing circuit 390 may also include a memory that stores data that cannot be transmitted.

Processing circuit 390 then transfers the data to receiving device 334 using wired transmitter 350 or wireless transmitter 354. Preferably, acquisition device 372 can transmit data using wired transmitter 350 in a wired data transmission mode 351 and transmit data using wireless transmitter 354 in a wireless data transmission mode 355. Processing circuit 390 may be able to determine whether wired transmitter 350 is coupled to receiving device 334. If wired transmitter 350 is coupled to receiving device 334, then processing circuit 390 may transmit data in a wired data transmission mode 351. If wired transmitter 350 is not coupled to receiving device 334, then processing circuit 390 may transmit data in a wireless data transmission mode 355. Alternately, processing circuit 390 may receive an input from user interface 362 that determines which data transmission mode to use.

Wireless transmitter 354 may be a transmitter, a transceiver, or any other wireless transmitting device. Wireless transmitter 354 preferably uses a technology not requiring a line of sight, such as RF technology. Also, wireless transmitter 354 preferably uses a technology that automatically detects the presence of other wireless devices that are in the vicinity of wireless transmitter 354. Even more, wireless transmitter 354 would suitably use a technology that requires only a small amount of power. Transmitter 354 may use Bluetooth™ technology, 802.11b protocol, WMTS protocol, or some other wireless technology.

The Bluetooth trademark is owned by Bluetooth SIG, Inc. Bluetooth wireless technology provides wireless connections; enabling links between mobile computers, mobile phones, portable handheld devices, and connectivity to the Internet. Bluetooth devices tend to have a low power consumption and a low cost.

The Bluetooth wireless specification includes both link layer and application layer definitions for product developers which supports data, voice and content-centric applications. Radios that comply with the Bluetooth™ wireless specification operate in the unlicensed, 2.4 GHz ISM (Industrial, Scientific and Medical) Band radio spectrum. These radios use a spread spectrum, frequency hopping, full-duplex signal at up to 1600 hops/sec. The signal hops among 79 frequencies at 1 MHz intervals to give a high degree of interference immunity. Bluetooth's synchronous bands are geared to carry relatively high-quality voice, while the asynchronous communication will support data at slightly more than 700 Kbps.

Distance for standard devices is limited to about 10 meters, but can be expanded to much larger distances (such as 100 meters) if desired. Once the devices are within the distance boundary, the devices can be connected automatically. It also provides a fast and secure transmission of voice and data even when the devices do not have a line of sight.

WTMS (or Wireless Medical Telemetry Service) generally operates in a frequency band of 608–614 Mhz, 1395–1400 MHz, or 1429–1432 MHz and may use a protocol such as that described in U.S. Pat. No. 5,944,659. The WTMS is a band reserved almost exclusively for medical devices, and, as a result, should not suffer from intentional interference from other bands. Under current FCC guidelines, voice and video communications are not allowed to be transmitted using the WTMS bands, but patient data may be transmitted.

Acquisition device 372 also includes a user interface 362. User interface 362 may include user inputs that allow a user to enter commands or other data, may include displays that indicate system function and/or subject parameter data, and/or may include alarms that indicate the occurrence of an event.

Acquisition device 372 may also include a battery 366. Battery 366 is preferably a rechargeable battery that powers acquisition device 372 when in a wireless data transmission mode 355, and is recharged when in a wired data transmission mode. Battery 366 may be configured to be removable by using a battery slot.

Acquisition device 372 may also include an expansion port that allows additional resources to be connected. Also, acquisition device 372 may include an output control 358 that controls the operation of an external device.

Receiving device 334 receives data from acquisition device 372 with wireless receiver 342 and/or using wired receiver 336. Wireless receiver 342 may be a receiver, a transceiver, or some other type of receiving device. Data received by wired receiver 336 and wireless receiver 342 is sent to processing circuit 392. Processing circuit 392 can digitize the data, can filter the data, can analyze the data, can separate the data, and/or can process the data in some other manner. Data from processing circuit 392 can be output to host 341 using outputs 340 and/or can be transferred across a network using network interface 339.

Hosts 341 can be individual devices which display and/or control different parameters. For example, one host may display or process cardiac output, another may display or process ECG, yet another may display or process SpO2, etc. Alternatively, host 341 may be a display for displaying information processed by acquisition device 372 and/or receiving device 334, may process a plurality of parameters, may monitor for alarms, etc. Each host 341 may receive identical data. Alternatively, each host 341 may receive data from a particular sensor 370. This may be accomplished by correlating an input 356 to an output 340. Alternatively, this may be accomplished by identifying the type of sensor and/or the type of monitor connected to input 356 and output 340 respectively. Further, each host 341 may receive a unique combination of sensor outputs and/or processed data.

Referring to FIG. 5, a data acquisition device 472 includes a housing 494. Housing 494 is configured to be small and compact such that it is easier to transport. Housing 494 may also contain clips or other devices that allow it to be wearable by a patient. As an alternate to clips, housing 494 may be configured to be received in a carrying case that is wearable by a user.

Acquisition device 472 includes inputs 456 that receive cables 470 extending from sensors that are coupled to a subject. Acquisition device 472 also includes a user interface 462. User interface 462 can include LEDs that indicate the status of acquisition module 472 (tethered/untethered, battery low/charging/full, etc.). User interface 462 can also include a power button, calibration buttons, or some other user input device.

Referring to FIG. 6, data is received from sensors coupled to a subject at block 500. The data can be high acuity patient parameter data. High acuity patient parameter data includes any parameter set that is typically used to monitor high acuity patients, but not regularly used to monitor other patients such as sub-acute patients. High acuity patients are patients who have a patient:clinician ratio of at most 3:1 and typically less. Clinicians can include doctors, nurses, physical therapists, physician assistants, etc. Some examples of high acuity parameter sets include those that use invasive techniques, an ECG having at least three leads (especially those having ten or more leads), parameter sets including four or more separate parameters, etc. Some examples of patient parameters include blood pressure, cardiac output, temperature, blood oxygen saturation, respiration rate, ECG data, etc.

The data may be processed at block 504. Processing the data could include combining the data into a packet signal, analyzing the data, filtering the data, converting the data to digital signals, and/or some other type of processing. Data can then be displayed at block 506, an alarm can be sent at block 502, and/or an external device can be actuated at block 507. External devices coupled to patients can include an intra-aortic balloon pump, a defibrillator, and/or some other external medical device. The external device can also be actuated at block 507 based on a signal input at block 505. The signal at block 505 may be input from a network, from a monitor, from a receiving device, and/or from some other stimulus.

Data processed at block 508 may then be transferred at block 510 or 514 based on a determination of the data transmission mode at block 508. The determination at block 508 can be made based on a position of a switch, some other user input, an external input, on whether a wired connection is being made to a receiving device, and/or some other condition. The data transition mode may be switched from a tethered data transmission mode to an untethered data transmission mode by a user input, or automatically.

If data is to be transferred in a tethered data transmission mode, data is transferred at block 510. If data is to be transferred in an untethered data transmission mode, data is transmitted wirelessly at block 514. Wirelessly transmitted data can be transmitted point-to-point to a local host via a receiving device connected to the local host, or can be transferred over a network. Wireless data may generally be transferred point-to-point, but, if the acquisition device leaves the vicinity of the local/bedside host, data may be transferred over a network.

A single transmitter may be used for both point-to-point and network data transmission, or two different transmitters may be used, such as a transmitter using Bluetooth technology for point-to-point transmission, and a transmitter using WiFi technology for network transmission. The untethered data transition mode may be switched between a point-to-point mode and a network mode manually or automatically (i.e. when a Bluetooth receiving device is or no longer is detected to be in proximity). Still further, an acquisition device may be configured to use only one type of untethered data transmission mode.

Data may also be transmitted in a single mode such as the untethered data transmission mode. In this case, the acquisition device would preferably still be connectable to a power supply such that a rechargeable battery may be recharged while a subject is still being monitored.

Data is preferably transmitted continuously. Continuously transmitting means that data is generally transmitted in real-time. Continuously transmitting is not meant to mean that data is always being transmitted. For instance, a device may run out of power, be shut off, become out of range, not switch between a tethered and untethered mode of operation very quickly (for instance, if the switching requires a user to flip a switch), may switch from a continuous untethered data transmission mode to a tethered transmission mode, or lose the ability to transmit in real time by some other means. While these situations may temporarily impair the ability of the data to be transmitted, the data is still generally being transmitted in real-time, and thus continuously. A short delay, a buffer, or a temporary lapse between acquisition and transmission of data does not prevent the data from being considered as substantially continuous.

If data is unable to be transmitted, it may be stored at block 512 and then transferred at block 510 or 514 at a later point in time.

Data is then received at block 516. The data is preferably received by a local host, such that blocks 516, 518, and 526 would occur at the local host. Alternatively, an adapting device may receive the data, and then transfer the data to the local host. The received data can be processed (or further processed) at block 518. Processing the data at block 518 can include separating the data from a packet signal, analyzing the data, filtering the data, converting the data to digital signals, and/or some other type of processing.

Data processed at block 518 can be transferred across a network at block 520 or to a local/bedside host (a host in the vicinity of the subject and the acquisition device) at block 526. Data transferred to a network at block 520 may be further processed at block 528, may be used to generate an alarm at block 532, and may be transferred to a local host at block 526. Data transferred to a local host may be processed at block 530, displayed at block 534, and used to generate an alarm at block 532.

Data transferred to a network at block 520 may be stored at block 522, such as in the form of a record in a patient or health care facility file. Data may also be used to generate a bill at block 524.

A bill generator can generate a bill based on the use of a monitor at block 524. The bill generator can generate a bill for the use of the monitoring system, or can integrate the use of the monitoring system into a larger bill to be sent. The bill generator can also monitor the usage of the monitoring system, and generate reports based on usage of the monitoring system. The bill generator can also be used to send a notice to a person across a network indicating that the monitoring system is being used and billed, and/or that a patient is experiencing medical trouble. People that may desire receiving such a notice might include a patient's primary physician, a treating physician, an insurance carrier, and a patient. Delivering a notice to an insurance carrier may allow faster approval for sudden, unexpected usage of the monitoring system, and/or other medical treatment. This would allow a hospital to collect funds sooner, and would allow a patient to worry less about obtaining coverage after treatment. This can also allow medical facility staff and insurance staff to make more informed business decisions. Once the bill is generated, it can then be sent physically or electronically to a recipient. The recipient may be a computer at an insurance company that calculates the extent of coverage and the amount to be paid based on the usage of the monitoring system, or some other recipient.

The invention has been described with reference to various specific and illustrative embodiments and techniques. However, it should be understood that many variations and modifications may be made while remaining within the spirit and scope of the invention. For instance many of the components and sub-components from acquisition devices 72, 372, and 472, receiving devices 20, 34, and 334, and other listed components can be rearranged, removed, formed as separate units which are later coupled, and/or formed into integrated units, and still remain within the scope of the invention. For instance, a high acuity acquisition device could be comprised of a handful (three or fewer) separate devices which together can be used to monitor a high acuity parameter set.

What is claimed is:

1. A monitoring system, comprising:
    an acquisition device, the acquisition device comprising,
        an input configured to receive data from a plurality of sensors coupled to a patient, and
        a wireless transmitter that continuously transmits data received by the input; and
    a receiving device, the receiving device comprising,
        a receiver that receives the data transmitted by the acquisition device, and
        an output from the receiver that outputs the data to a least one local host;
    wherein the system transmits data from the data acquisition device to the receiving device point-to-point when the receiving device is within a transmission range, and further wherein the system transmits data from the data acquisition device to the receiving device through a network when the receiving device is not within the transmission range.

2. The monitoring system of claim 1, wherein the acquisition device comprises a plurality of inputs configured to receive data, from sensors coupled to the patient.

3. The monitoring system of claim 2, wherein the acquisition device may be switched between a tethered data transmission mode and an untethered data transmission mode.

4. The monitoring system of claim 3, wherein the data acquisition device further comprises a housing configured to be wearable by a patient.

5. The monitoring system of claim 2, wherein
    a first input of the acquisition device is configured to receive data from a sensor associated with a type of monitoring, the type of monitoring selected from a group consisting of electrocardiography, pulse oximetry, cardiac output, end tidal carbon dioxide, invasive blood pressure, non-invasive blood pressure and temperature; and
    a second input of the acquisition device is configured to receive data from a sensor associated with a type of monitoring, the type of monitoring selected from a group consisting of cardiac output, end tidal carbon dioxide, invasive blood pressure, non-invasive blood pressure, and temperature.

6. The monitoring system of claim 2, wherein the plurality of inputs of the acquisition device are configured to receive data from at least three different types of sensors monitoring at least three different parameters.

7. The system of claim 2, wherein the plurality of inputs of the acquisition device are configured to receive data from at least five different types of sensors monitoring at least five different parameters.

8. The monitoring system of claim 2, wherein the receiving device further comprises an alarm.

9. The monitoring system of claim 1, wherein the acquisition device may be switched between a tethered data transmission mode and an untethered data transmission mode.

10. The monitoring system of claim 9, wherein switching the, acquisition device between a tethered data transmission mode and an untethered data transmission mode is facilitated by an output on the data acquisition device that allows data and power to be transmitted over a single connection.

11. The monitoring system of claim 1, wherein the acquisition device further comprises a control output configured to allow the acquisition device to control an external device coupled to the patient.

12. The monitoring system of claim 11, wherein the control output is configured to control an external device selected from the group consisting of an intra-aortic balloon pump and a-defibrillator.

13. The monitoring system of claim 11, wherein the receiving device is a portion of the local host.

14. A wearable acquisition device for use with high acuity patients, comprising:
    at least three inputs that are configured to receive data from a plurality of sensors coupled to a patient that are monitoring at least three different parameters;
    a wireless transmitter that transmits data received by the inputs; and
    a receiver configured to receive the transmitted data and output the data to at least one local host such that the acquisition device transmits to the receiver point-to-point when the receiver is within a transmission range, and further wherein the device transmits data to the receiver through a network when the receiver is not within the transmission range.

15. The acquisition device of claim 14, wherein at least one of the inputs is configured to receive data from an invasive sensor.

16. The acquisition, device of claim 14, wherein the acquisition device may be switched between a tethered data transmission mode and an untethered data transmission mode.

17. The acquisition device of claim 14, wherein the data acquisition device further comprises a housing configured to be wearable by a patient.

18. The acquisition device of claim 14, wherein
    a first input of the acquisition device is configured to receive data from a sensor associated with a type of monitoring, the type of monitoring selected from a group consisting of electrocardiography, pulse oximetry, cardiac output, invasive blood pressure, end tidal carbon dioxide, non-invasive blood pressure, and temperature; and
    a second input of the acquisition device is configured to receive data from a sensor associated with a type of monitoring, the type of monitoring selected from a group consisting of cardiac output, invasive blood pressure, non-invasive blood pressure, end tidal carbon dioxide, and temperature.

19. The acquisition device of claim 14, wherein the inputs of the acquisition device are configured to receive data from at least five different types of sensors monitoring at least five different; parameters.

20. A wearable acquisition device for use with high acuity patients, comprising:
    an input that is configured to receive data from an invasive sensor coupled to a patient;
    a wireless transmitter that transmits data received by the inputs; and
    receiver configured to receive the transmitted data and output the data to at least one local host such that the acquisition device transmits to the receiver point-to-point when the receiver is within a transmission range, and further wherein the device transmits data to the receiver through a network when the receiver is not within the transmission range.

21. The acquisition device of claim 20, wherein the input is configured to receive data from an invasive sensor selected from the group consisting of an invasive blood pressure sensor, an invasive temperature sensor, and a cardiac output sensor.

22. The acquisition device of claim 20, further comprising a control output configured to allow the acquisition device to control an external device coupled to the patient.

23. The acquisition device of claim 20, wherein the control output is configured to control an external device selected from the group consisting of an intra-aortic balloon pump and a defibrillator.

24. An acquisition device, comprising: an input configured to receive data from at least one sensor coupled to a patient;
    a wired transmitter that transmits data received by the input in a tethered data transmission mode; and
    a wireless transmitter that transmits data received by the input point-to-point in an untethered data transmission mode in a point-to-point fashion when the wireless transmitter is within a transmission range, and through a network when the wireless transmitter is not within the transmission range;
    wherein the acquisition device has a data transmission mode that is switchable between the tethered data transmission mode and the untethered data transmission mode.

25. The acquisition device of claim 24, further comprising
    a wired output slot, coupled to the wired transmitter, configured to receive a wire that facilitates wired transmission of data,
    a processing circuit that switches the data transmission mode between thee tethered data transmission mode and the untethered data transmission mode when a connection of the wired output slot is made or broken.

26. The acquisition device of claim 24, further comprising a wired output slot, coupled to the wired transmitter, configured to receive a wire that facilitates wired transmission of data and configured to simultaneously receive power from a power source.

27. The acquisition device of claim 24, wherein the wireless transmitter transmits a radio frequency signal.

28. The acquisition device of claim 27, wherein the wireless transmitter transmits signals using a protocol that allows devices within proximity to each other to connect automatically.

29. The acquisition device of claim 28, wherein the wireless transmitter uses Bluetooth technology.

30. The acquisition device of claim 24, further comprising a rechargeable battery adapted to recharge when the data transition mode is in a tethered data transition mode.

31. The acquisition device of claim 24, further comprising a control circuit configured to switch the data transmission mode between the tethered data transmission mode and the untethered data transmission mode such that data transmission is substantially continuous.

32. The acquisition device of claim 24, wherein the wireless transmitter transmits data using a technology that does not require line-o sight to transmit data.

33. The acquisition device of claim 24, further comprising a control, output configured to allow the acquisition device to control an external device coupled to the patient.

34. The acquisition device of claim 24, wherein the wireless transmitter is configured to transmit data point to point in the untethered data transmission mode.

35. The acquisition device of claim 24, wherein the acquisition device is configured to be wearable by the patient.

36. A data acquisition system for use with high acuity patients, comprising:
   an acquisition device, the acquisition device comprising;
      a plurality of inputs configured to receive data from a plurality of sensors coupled to a patient,
      a wired transmitter that transmits data received by the inputs,
      a wireless transmitter that transmits data received by the inputs, the, wireless transmitter using a technology that does not require a line of sight to transmit data, and
      a housing carrying at least some of the components of the acquisition device, the housing configured to be portable by a patient, wherein the acquisition device has a data transmission mode that is switchable between a tethered data transmission mode and an untethered data transmission mode; and
   a receiving device, the receiving device comprising;
      a receiver that receives data transmitted by the acquisition device,: and
      an output from the receiver that outputs data to at least one local host, wherein the system transmits data from the data acquisition device to the receiver point-to-point when the receiver is within a transmission range, and further wherein the device transmits data to the receiver through a network when the receiver is not within the transmission range.

37. The device, of claim 36, wherein
   a first input of the acquisition device is configured to receive data from a sensor associated with a-type of monitoring the type of monitoring selected from a group consisting of electrocardiography, pulse oximetry, cardiac output, end tidal carbon dioxide, invasive blood pressure, non-invasive blood pressure, and temperature; and
   a second input of the acquisition device is configured to receive data from a sensor associated with a type of monitoring, the type of monitoring selected from a group consisting of cardiac output, end tidal carbon dioxide, invasive blood pressure, non-invasive blood pressure, and temperature.

38. The system of claim 36, wherein at least one of the plurality of inputs is configured to receive data from an invasive sensor coupled to a patient.

39. The system of claim 36, comprising a plurality of local 10 monitors that receive data from the acquisition device by way of the receiving device.

40. The system of claim 36, wherein the housing is configured to be wearable by a patient.

41. The system of claim 36, wherein the receiving device is a portion- of the local host.

42. A method for monitoring a patient, comprising:
   receiving data relating to high acuity parameters from sensors coupled to the patient;
   continuously transmitting the data to a local host; and
   transmitting the data point-to-point in an untethered data transmission mode when the local host is within a transmission range and further wherein the transmitting step is effectuated through a network when the local host is not within the transmission range.

43. The method of claim 42, further comprising changing a data transmission mode from a tethered data transmission mode to the untethered data transmission mode.

44. The method of claim 42, wherein
   the high acuity parameters comprise at least a first high-acuity parameter and a second high acuity parameter;
   the first high acuity parameter selected from a group consisting of electrocardiograph information, blood oxygen saturation information, cardiac output, invasive blood pressure, non-invasive blood pressure, end tidal carbon dioxide, and temperature; and
   the second high acuity parameter selected from a group consisting of-cardiac-output, end tidal carbon dioxide, invasive blood pressure, non-invasive blood pressure, and temperature.

45. The method of claim 42, wherein at least one sensor is an ECG having at least three leads.

46. The method of claim 42, wherein at least one sensor is an ECG having, at least ten leads.

47. The method of claim 42, wherein the, high acuity parameters include at least four different parameters.

48. The method of claim 42, wherein the high acuity parameters comprise ECG blood oxygen saturation,; and at least one other parameter.

49. The method of claim. 42, further comprising transmitting the data to a monitor over a network.

* * * * *